United States Patent [19]

Sahagen

[11] Patent Number: 5,510,895
[45] Date of Patent: Apr. 23, 1996

[54] PROBE FOR MONITORING A FLUID MEDIUM

[76] Inventor: Armen N. Sahagen, 16757 Bolero La., Huntington Beach, Calif. 92649

[21] Appl. No.: 26,987

[22] Filed: Mar. 5, 1993

[51] Int. Cl.$^6$ .............. A61B 5/00; H01J 40/14; G01L 7/08
[52] U.S. Cl. .............. 356/436; 356/72; 128/667; 128/665; 73/715
[58] Field of Search .............. 356/72, 128, 436; 250/231.11; 128/667, 665; 73/705, 714, 715, 722

[56] References Cited

U.S. PATENT DOCUMENTS

| | | | |
|---|---|---|---|
| 3,654,579 | 4/1972 | Kurtz et al. | 338/2 |
| 4,085,620 | 4/1978 | Tanaka | 73/727 |
| 4,127,840 | 11/1978 | House | 338/4 |
| 4,166,384 | 9/1979 | Matsuda et al. | 73/141 A |
| 4,444,516 | 4/1984 | Dostoomian et al. | 74/131 |
| 4,487,206 | 12/1984 | Aagard | 128/667 |
| 4,569,570 | 2/1986 | Brogårdh et al. | 350/96.34 |
| 4,589,286 | 5/1986 | Berthold, III | 73/715 |
| 4,600,912 | 7/1986 | Marks et al. | 338/42 |
| 4,611,600 | 9/1986 | Cohen | 128/667 |
| 4,670,649 | 6/1987 | Senior et al. | 250/227 |
| 4,689,483 | 8/1987 | Weinberger | 250/231 R |
| 4,691,575 | 9/1987 | Sonderegger et al. | 73/756 |
| 4,771,638 | 9/1988 | Sugiyama et al. | 73/721 |
| 4,787,396 | 11/1988 | Pidorenko | 128/667 |
| 4,803,992 | 2/1989 | Lemelson | 128/667 |
| 4,824,206 | 4/1989 | Klainer et al. | 350/96.29 |
| 4,893,935 | 1/1990 | Mandel et al. | 356/436 |
| 4,909,588 | 3/1990 | Harner et al. | 350/96.20 |
| 4,970,903 | 11/1990 | Hanson | 73/862.59 |
| 4,994,680 | 2/1991 | Brügmann | 250/227.11 |
| 4,994,781 | 2/1991 | Sahagen | 338/47 |
| 5,088,329 | 2/1992 | Sahagen | 73/727 |
| 5,107,847 | 4/1992 | Knute et al. | 73/705 |
| 5,146,083 | 9/1992 | Zuckerwar et al. | 250/227.21 |
| 5,206,711 | 4/1993 | Berthold et al. | 356/436 |
| 5,241,368 | 8/1993 | Ponstingl et al. | 356/73 |
| 5,280,788 | 1/1994 | Janes et al. | 128/665 |
| 5,313,957 | 5/1994 | Little | 128/667 |

FOREIGN PATENT DOCUMENTS

| | | |
|---|---|---|
| 0189492 | 8/1986 | European Pat. Off. |
| 0336437 | 10/1989 | European Pat. Off. |
| 1548380 | 10/1968 | France |
| 2940955 | 4/1981 | Germany |

OTHER PUBLICATIONS

Pierre Desgoutte et al., *Les capteurs en instrumentation industrielle* (no translation provided).
Cross, *Practical Infra-Red Spectroscopy* at 36 (1964) [copy not readily available].

*Primary Examiner*—Rolf Hille
*Assistant Examiner*—David B. Hardy
*Attorney, Agent, or Firm*—Stetina Brunda & Buyan

[57] ABSTRACT

A probe for monitoring a fluid medium employing at least one electromagnetic wave reflector and at least one fiber optic for analysis of the fluid medium. The probe includes a base having a hole, a window covering the hole of the base, wherein the window transmits electromagnetic waves and a electromagnetic reflector, spaced apart from the window, disposed to reflect at least part of the electromagnetic waves toward the window. The probe collects the reflected waves through one or more fiber optics placed behind a window to a fluid medium and transmits the waves to a spectrometer connected to a computer which analyzes the fluid medium on a real time on-line basis. Piezoresistive and temperature sensing elements are deposited on the window which also may function as a force collector diaphragm of thin refractory or a semiconductor materials. The piezoresistive elements are on the unsupported part of the diaphragm and at least part of the diaphragm is transparent to electromagnetic waves.

83 Claims, 5 Drawing Sheets

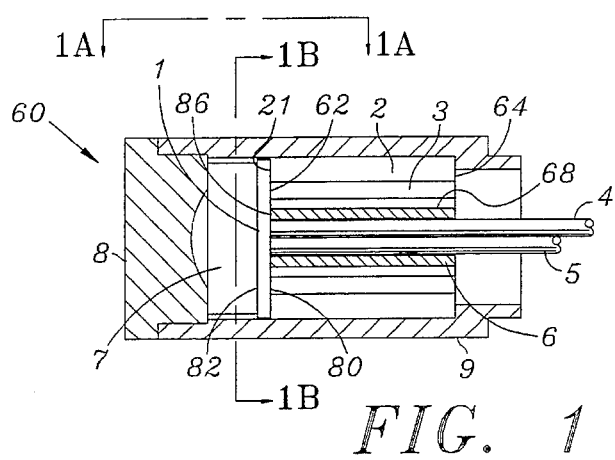
FIG. 1
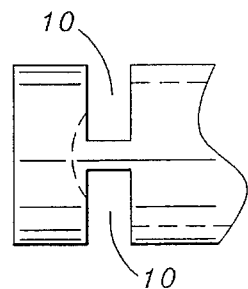
FIG. 1A
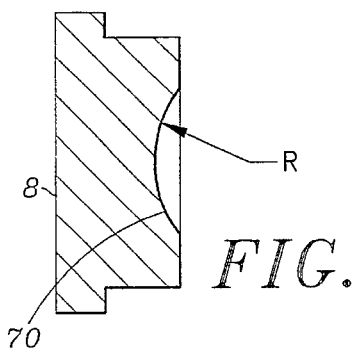
FIG. 2A
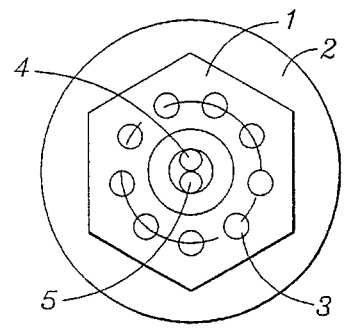
FIG. 1B
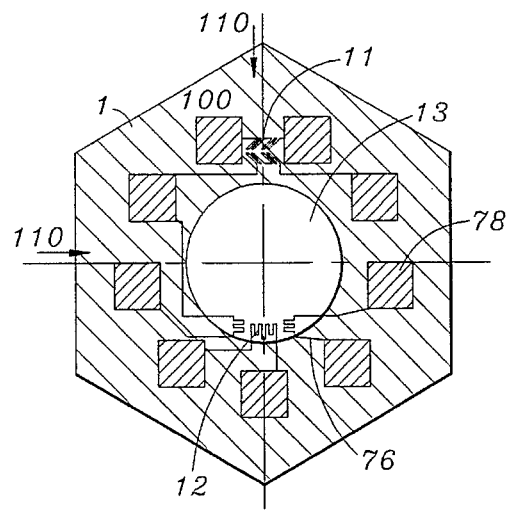
FIG. 3
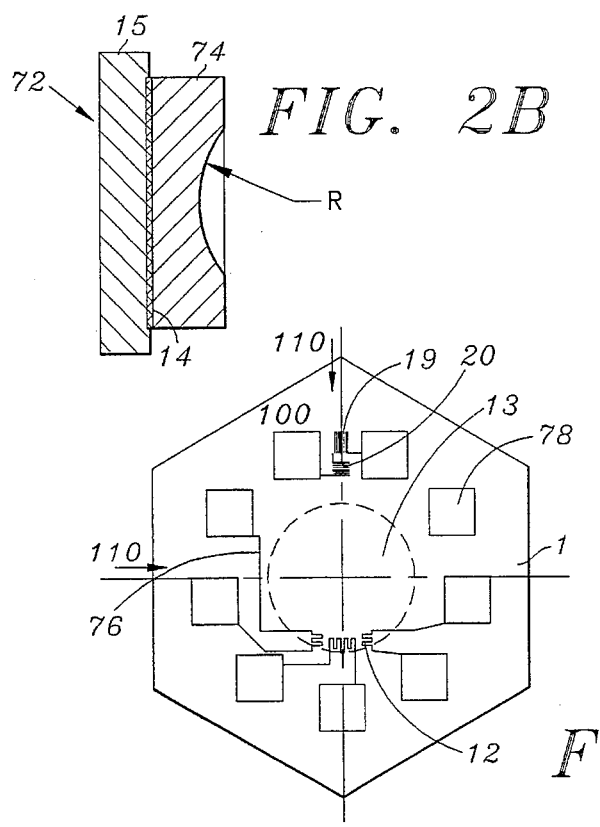
FIG. 2B
FIG. 5

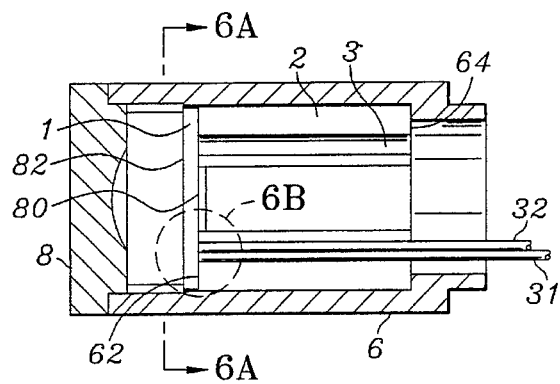
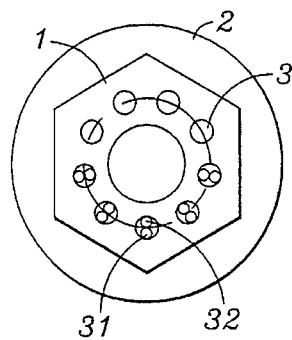
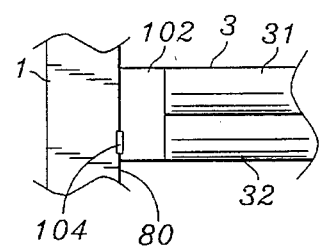
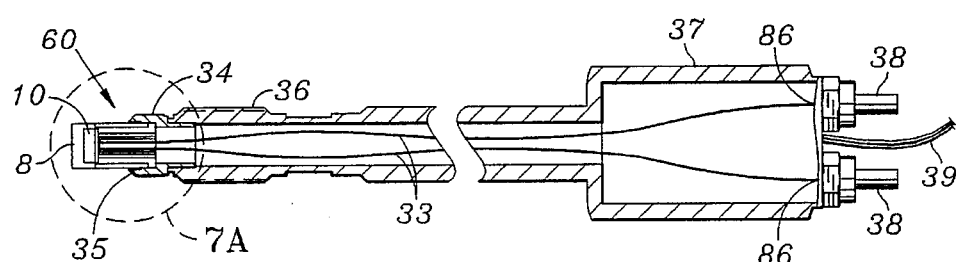
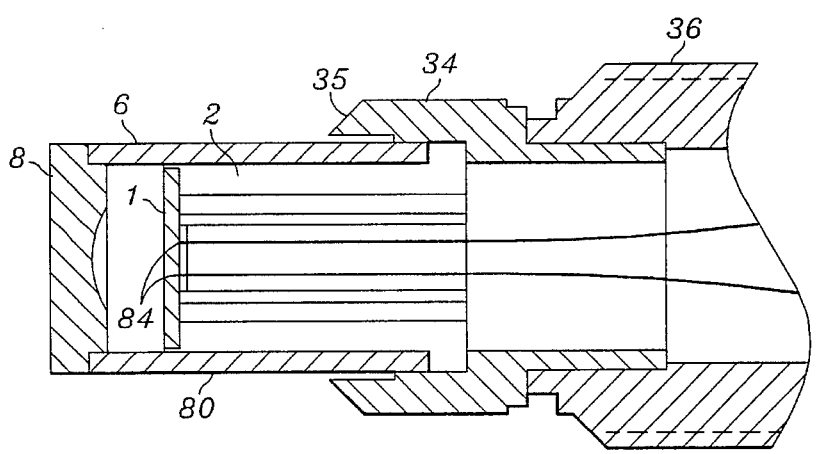

PROBE FOR MONITORING A FLUID MEDIUM

BACKGROUND OF THE INVENTION (1) Field of the Invention

The present invention relates to a probe for monitoring a fluid medium. More specifically, the invention relates to a probe for monitoring a fluid medium employing at least one electromagnetic wave reflector and at least one fiber optic for analysis of the fluid medium.

(2) Description of the Related Art

Certain applications exist in industry for real-time on-line monitoring of fluid medium. For example, in the polymer industry to monitor the temperature and pressure and composition of a polymer melt would be highly desirable. In other industries, involving chemical processing plants, oil refinery and distillation plants, smog and pollution detection and medical on-line monitoring of the pressure, temperature and composition of the fluid mediums can be essential. Specifically, monitoring the composition of the polymer melt may include a quantitative and qualitative analysis of the elements, compounds and/or mixtures making up the polymer melt. However, apparently no existing probe can do such monitoring under these conditions. At best, the industry employs piezoresistive pressure transducers to monitor the high pressure and temperatures of polymer melts such as those described in U.S. Pat. Nos. 4,994,781 and 5,088,329 to Sahagen.

Such piezoresistive pressure transducers employ a pressure force collector diaphragm having one or more piezoresistive elements mounted thereon. The diaphragm with the piezoresistive elements is typically placed in a pressure cell base which maintains a low pressure or vacuum on one side of the diaphragm. External fluid medium under pressure contacts the other side of the diaphragm. A voltage is placed across the piezoresistive element(s) and as the diaphragm flexes in response to a pressure changes, a resistance change in the piezoresistive element(s) results in a change in the current flowing through the piezoresistive element(s).

Apparently, however, there is no on-line monitoring of the composition of polymers or other fluid medium at high temperatures and pressures. Thus, the composition of the polymer melts are not known on a real time basis at high temperatures and pressures. The pressure and temperature of such polymer melts can reach up to 15,000 psi and to 800° F. and above. In fact, in some polymer melt processes the temperature may go up to 1500° F. or higher and the pressures up to 50,000 psi. Furthermore, in certain applications, the polymer melt will be a slurry viscous fluid having corrosive and abrasive properties which readily abrade and degrade conventional steel alloys and stainless steel posing additional obstacles to monitoring the polymer.

As a result, in the polymer industry, the polymer melt process is controlled by off-line sampling. The composition of the polymer melt is typically analyzed on a regular basis by extracting a sample of the polymer melt from the process for laboratory analysis. After analysis, a decision is made whether the polymer melt is suitable for production. Because such a laboratory analysis can require as much as four hours to perform off-line sampling can result in the production of considerable material not useful for its intended purpose. A large-scale polymer melt processing plant can generate in excess of $100,000 worth of polymer per hour. Thus, effective on-line monitoring of a high temperature and pressure polymer melt can result in large cost savings by preventing the waste of a large amount of material from which the polymer is derived on a monthly basis in one plant alone. Thus, a probe performing real time on-line monitoring of not only the pressure and temperature, but also the composition of the polymer melt would be highly desirable. Accordingly, there is a great need in the polymer industry for a durable reliable probe which can monitor the high pressure, high temperature, composition and other physical properties of polymer melts.

In addition, there is a great need in the medical world for monitoring blood, cancer, and abnormal cell growth within the body without the need for major surgery. For example, sometimes surgery must be performed to determine the stage or growth rate of cancer. When cancer is bombarded by certain electromagnetic waves, it will radiate scattered waves or luminescence waves which can be collected and analyzed. The characteristics of such waves will indicate the concentration, growth rate, and other important properties of the cancer. It would be highly desirable to have a probe which can use this phenomena to monitor cancer.

One technique for treatment of cancer in an internal organ involves irradiating the patient's body. Eradicating such cancerous growth can require irradiating both the affected organ and the surrounding tissue with high dosages of radiation. This is because the radiation must penetrate surrounding tissue, bodily fluids and perhaps other organs. This can have an adverse effect on the patient receiving the dosage, which in turn drastically limits the amount and corresponding effectiveness of the dosage.

SUMMARY OF THE INVENTION

The present invention provides a probe suitable for use in determining the pressure, temperature and composition simultaneously or individually of corrosive and abrasive materials or other fluid mediums in a wide variety of other extreme environments.

The present invention further provides a probe for monitoring a fluid medium, including a base having a hole, a window covering the hole of the base, the window being capable of transmitting electromagnetic waves, and a electromagnetic reflector, spaced apart from the window, disposed to reflect at least part of the electromagnetic waves toward the window.

In another embodiment, the present invention provides means to transmit electromagnetic waves into a fluid medium and collect the waves reflected or dispersed from the fluid medium. Such fluid medium may be extremely corrosive, abrasive, at high temperatures and high pressures, either simultaneously or separately.

In another embodiment, the present invention provides means for emitting electromagnetic waves into the fluid medium, where the electromagnetic waves bounce back after penetration into the fluid medium through dispersion and/or reflection from a electromagnetic reflector placed in the path of the fluid medium.

In another embodiment, the present invention collects dispersed or reflected electromagnetic waves through a fiber optic placed behind a window to a fluid medium and transmits the waves to a spectrometer operably connected to a computer which analyzes the fluid composition on a real time on-line basis.

In another embodiment, the present invention, provides means for analyzing the composition and monitoring the pressure and temperature of the fluid medium either simultaneously or individually. Pressure and temperature sensing elements are placed on areas of a force collector diaphragm of, for example, a thin crystalline or amorphous refractory or semiconductor materials. The elements are place on the diaphragm so as to leave a portion of the diaphragm open for the transmission and collection of electromagnetic waves.

In another embodiment, the present invention provides a window transparent to certain electromagnetic waves therefore allowing certain wavelength bands such as in the infrared spectrum, near-infrared, medium infrared, to be filtered by the window.

In another embodiment, the present invention provides a probe having means for electromagnetic waves to be transmitted into the fluid medium and reflected back to the means by a reflector facing the means. The electromagnetic waves are collected through a fiber optic placed behind the means. Such means make the probe suitable for fluid mediums which are extremely corrosive, abrasive, and at high temperatures and high pressures. In addition, the reflector surface is non-adhesive to the fluid medium and maintains the integrity and reflectivity of the reflector.

The present invention further provides a force collector diaphragm which acts as a window to isolate the high pressure, high temperature fluid medium from the outside world and as a lens to collect reflected or scattered waves more efficiently.

The present invention also provides means to monitor or measure the concentration of known element(s), compound(s), compound additive(s) or mixtures in a fluid medium individually or collectively. This is accomplished through having access to a plurality of individual electromagnetic wave windows, wherein waves within a narrow bandwidth are transmitted or collected in order to identify and measure the concentration(s).

The present invention further provides means wherein fiber optics are kept under compression against the window therefore compensating for any difference in the thermal expansion or contraction of the fiber optic and overall assembly due to temperature variation.

The present invention further provides means for transmitting a concentrated dosage of electromagnetic radiation to a local region in a manner which renders the radiation effective and promotes local disintegration, eradication and treatment of cancerous growth. The present invention further provides means for simultaneously applying the radiation and monitoring the results such that it is possible to administer larger doses of radiation at more frequent intervals.

The present invention provides a combination probe capable of monitoring and eradicating cells in the human body by providing means for monitoring radiation on a real-time on-line basis by collecting luminescence, reflected or scattered waves after interaction and irradiation of the cells.

The present invention further provides an improved fiber optic capable of transmitting and collecting electromagnetic waves of a broader wavelength range than provided by conventional fiber optics.

BRIEF DESCRIPTION OF THE DRAWINGS

The foregoing objects, features and advantages of the invention will become more apparent from the following detailed description of the preferred embodiments taken in conjunction with the accompanying drawings, in which:

FIG. 1 is a cross-section through an embodiment of the probe of the present invention.

FIG. 1A is a view of the probe of FIG. 1 taken along line A—A.

FIG. 1B is a sectional end view of the probe of FIG. 1 taken from the fluid medium side along line B—B.

FIG. 2A is a cross-section of an embodiment of the electromagnetic wave reflector.

FIG. 2B is a cross-section of an embodiment of a electromagnetic wave reflector where material transparent to electromagnetic waves protects an embedded reflector surface from the fluid medium.

FIG. 3 illustrates an arrangement of contact pads, connecting arms, piezoresistive elements in a Wheatstone bridge and temperature sensing elements on the cavity side of the diaphragm.

FIG. 5 illustrates an arrangement of contact pads, connecting arms and an arrangement of the piezoresistive elements in a Wheatstone bridge and of the temperature sensing elements on the cavity side of the diaphragm.

FIG. 6 is a cross-section of an electromagnetic window embodiment of the probe permitting individual or simultaneous analysis of elements, compounds and/or mixtures.

FIG. 6A is an end view of the probe taken from the fluid medium side along line A—A of FIG. 6.

FIG. 6B is close up view of an alternative embodiment of a fiber optic air and a temperature sensitive element taken from the fluid medium side at section B of FIG. 6.

FIG. 7 illustrates the location of the fiber optics within the probe.

FIG. 7A is a close up of the probe taken at section A of FIG. 7. It illustrates fiber optics making contact with the diaphragm, the threads of the probe generating stress on the diaphragm and an isolation slot to reduce the stress.

DETAILED DESCRIPTION OF THE PREFERRED EMBODIMENTS

Figure 4:
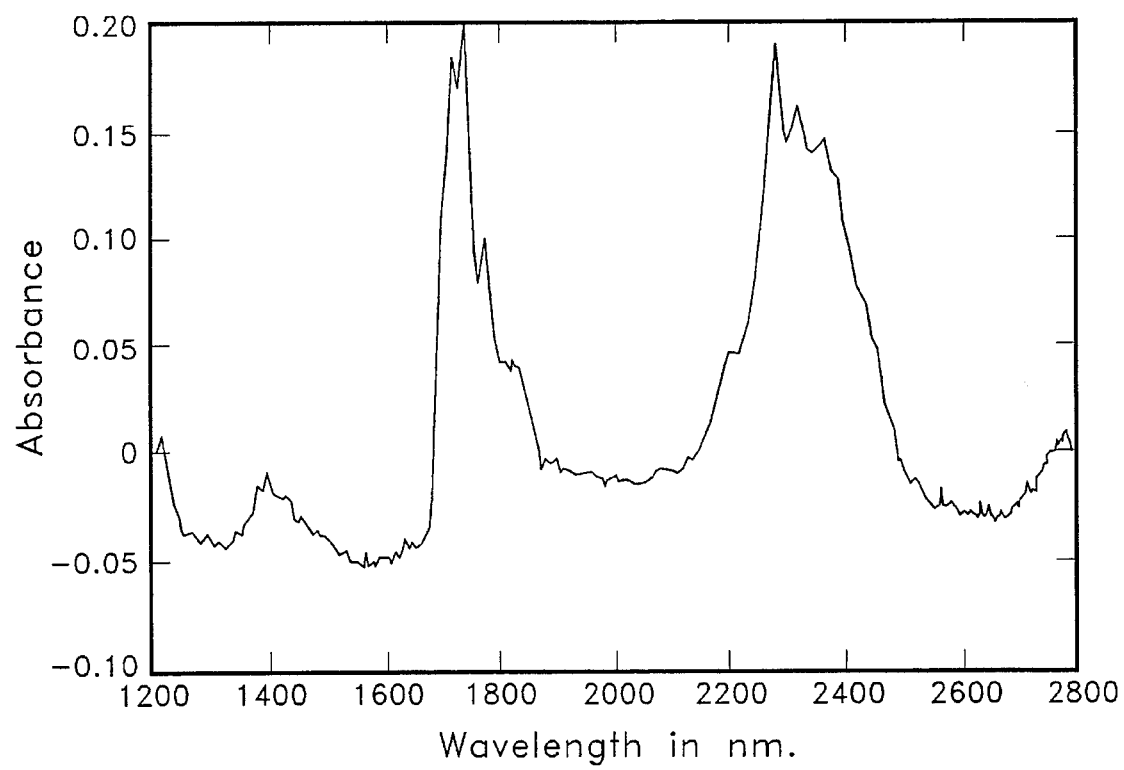
FIG. 4 is an absorption curve.

The following description is the best contemplated mode of carrying out the invention. The description is made for the purpose of illustrating the principles of the invention and should not be taken in a limiting sense. The scope of the invention is best determined by reference to the appended claims. In the accompanying drawings, like numbers designate like parts.

FIG. 1 of the drawings is a cross-section through a embodiment of the probe 60 of the present invention. The probe 60 includes a window 1 capable of transmitting electromagnetic waves. When the probe has a pressure monitoring function, the window 1 functions as a force collector diaphragm as described in U.S. Pat. Nos. 4,994,781 and 5,088,329 to Sahagen. These patents are hereby incorporated by reference. For brevity the window will be referred to as a force collector diaphragm 1. The diaphragm 1 can be made of crystalline or amorphous refractory material, semiconductor material, intermetallics or metal.

As shown in FIG. 1B, the diaphragm 1 is hexagonal, but may be circular, square, triangular or any other shape lending itself to ease of manufacture. The diaphragm 1 can be a thin deflectable single or polycrystalline sapphire of 0.003 to 0.070 inches thick. For example, single crystalline sapphire slices of 0.320 inch diameter and of 0.013 to 0.050 inches thickness may be used. The sapphire is preferably grown through the Czochralski process with a 1011 orientation along the C axis. A conventional process can be used to grow the epitaxial single crystal piezoresistive layers on the diaphragm 1.

Some other materials for diaphragm 1 are diamond, quartz and ceramic compounds such as $Al_2O_3$, better known as alumina; BeO beryllium oxide, better known as brylia; silicon nitride; silicon carbide compounds; BeO and $Al_2O_3$, brylia and alumina, better known as chrysoberyl; MgO and $Al_2O_3$, compounds, better known as spinel; zirconium oxide and alumina oxide systems, better known as zirconia alumina; $SiO_2$ and alumina compounds, better known as andalusite or silliminite; silicon nitrate and aluminum oxide compounds; and any other metal oxide compound or compound suitable for ceramic processing having a temperature coefficient of expansion of about $1\times10^{-7}$/°F. to $1\times10^{-3}$/°F., high electrical insulation properties and an optimized thermal conductivity of from 0.020 to 0.700 cal/cm²/cm/sec/°C.

As shown in FIG. 1, the diaphragm 1 is bonded by a bonding layer 21 to a pressure cell base 2 of amorphous or crystalline metal oxides, semiconductor material, metal, metal alloys or a combination thereof. The temperature coefficient of expansion of the base 2 should closely match that of the bonding layer 21 and of the diaphragm 1 to permit operation under high temperatures of up to 1500° F. and above and pressures of up to 50,000 psi and above. Preferably, the base 2 electrically isolates the electrical connectors (not shown) threaded through holes 3.

Alumina is a suitable material for the base 2. However, the base 2 can be other materials having the following properties: improved heat conductivity to minimize temperature response time, high dielectric constant; non-porous; good adhesion properties for glass ceramic and brazing sealing; and corrosion and abrasion endurance against corrosive environments and abrasive compounds which might be encountered in polymer, plastic, food and other industries.

Some other materials for base 2 are diamond, quartz, and ceramics such as BeO beryllium oxide, better known as brylia; silicon nitride; silicon carbide compounds; BeO and $Al_2O_3$, brylia and alumina, better known as chrysoberyl; MgO and $Al_2O_3$, compounds, better known as spinel; zirconium oxide and aluminum oxide systems, better known as zirconia alumina; $SiO_2$ and aluminum compounds, better known as andalusite or silliminite; silicon nitrate and aluminum oxide compounds; and any other metal oxide compound or compound suitable for ceramics processing having a temperature coefficient of expansion of about $1\times10^{-7}$/°F. to $1\times10^{-3}$/°F., high electrical insulation properties and an optimized thermal conductivity of from 0.020 to 0.700 cal/cm²/cm/sec/°C. Favorable results can be achieved when the temperature coefficient of expansion of the diaphragm 1 and base 2 substantially match.

The bonding layer 21 is preferably a ceramic glass with a working temperature of 1500° F. or higher. The bonding layer 21 can have temperature coefficient of expansion range of from $1\times10^{-7}$/°F. to $1\times10^{-3}$/°F. The ceramic glass also known as devitrifying glass can be used for bonding layer 21. Vitrifying or devitrifying glass can be applied to diaphragm 1 and base 2 on appropriate areas through conventional techniques such as silk screening or doctor blading. Some glass devitrifying compounds are commercially available from Corning Glass and other sources. One example is Corning Glass No. 7578.

After applying ceramic glass to diaphragm 1 and base 2 and a drying cycle, the ceramic glass will typically bond and seal the diaphragm 1 and base 2 at temperatures between 350° C. and 900° C. depending on the ceramic glass selected. At this temperature range, the ceramic glass goes through a nucleation and transformation stage and becomes a solid substance that, unlike glass, will not become plastic as temperature increases and will not melt at temperatures of up to 1200° C. Through selection of appropriate materials for the bonding layer 21, different temperature coefficients of expansion can be obtained to match that of diaphragm 1 and base 2. Matching the temperature coefficients of expansion of the diaphragm 1, base 2 and bonding layer 21 will reduce or eliminate microscopic cracks arising from repeated heating and cooling cycles occurring during operation of the probe 60.

As shown in FIG. 1B, the base 2 is cylindrical in shape. However, it also may be hexagonal, square, triangular or another shape lending itself to ease of manufacture. As shown in FIG. 1, the base 2 has an upper surface 62, a lower surface 64 and a hole 68 extending from the upper surface 62 to the lower surface 64. A cavity 66 is located along the upper surface 62.

Fiber optics 4 and 5 reside in an inner liner 6 which in turn resides in hole 68. The liner 6 is preferably of KOVAR. Fiber optics 4 and 5 are fixed together with the liner 6 by polyamide or another suitable high temperature material able to withstand the operating temperature of the probe 60. The resulting assembly facilitates the handling, housing, forming and polishing of the otherwise fragile fiber optics ends. The assembly permits the fiber optics 4 and 5 to slide in the hole 68 to compensate for temperature change when necessary as described below.

The diaphragm 1, base 2 and fiber optics 4 and 5 are housed in an external sleeve 9. The sleeve 9 is preferably made of KOVAR and fastens to the outside of base 2. Silver copper brazing, for example, can fasten sleeve 9 to base 2. The sleeve 9 strengthens base 2 which might be otherwise fragile and provides hermeticity. Additional housings and assemblies can be attached to sleeve 9 as necessary.

FIG. 1 illustrates that sleeve 9 extends beyond the diaphragm 1 and partially encloses an electromagnetic reflector 8. The reflector 8 is opposite fiber optics 4 and 5 ends at distance R. Favorable results have been achieved when the ends of the fiber optics 4 and 5 are placed at or in close proximity to the focal point.

Beer's law and Lambert's law express the relation of the intensity of the absorption to changes in concentration and sample thickness and can be used to calculate the appropriate path length from the reflector 8 to the end of the collecting fiber optic. Beer's law provides that the concentration of the fluid medium, its absorptivity and path length will equal a constant for a given transmittance. A.D. Cross, *Practical Infra-Red Spectroscopy* at 36 (1964) describes Beer's law and Lambert's law in more detail.

In one embodiment, fiber optic 4 emits electromagnetic waves into the fluid medium. The electromagnetic reflector 8 reflects some of the waves to the collecting fiber optic 5. Favorable results are achieved with a concave spherical shaped reflector 8. With this shape and an appropriate path length, the waves will converge at or near the end of collecting fiber optic 5. The reflector 8 may be concave, parabolic, a plane, cone-shaped, or even convex or any other shape reflecting electromagnetic waves to collecting fiber optic 5.

FIG. 1A is a view of the probe 60 of FIG. 1 taken along line A—A. Sleeve 9 includes two slots 10 opposite to each other and between the diaphragm 1 and the reflector 8. This arrangement permits the fluid to pass through a chamber 7 for monitoring and analysis (FIG. 1).

An electromagnetic wave source (not shown) sends electromagnetic waves into an end of fiber optic 4 which are transmitted and emitted from the opposite end of fiber optic 4 then through the diaphragm 1. The waves emitted from the diaphragm 1 enter the fluid medium in chamber 7 and impinge on the reflector 8. The waves are reflected back to the diaphragm 1 and enter collecting fiber optic 5. The collected waves are then transmitted through the fiber optic 5 and sent to the external world for analysis by a spectrometer or other analytical test equipment.

A fluid medium (e.g. gas or liquid) will differentially absorb over an electromagnetic wavelength range. The electromagnetic waves collected at the various wavelengths can be analyzed by a spectrometer. The spectrometer can generate an absorption curve depicting electromagnetic wave absorbance and reflectance curve having peaks and valleys as illustrated in FIG. 4. Any element, mixture, or compound will generate a different signature, that is, a transmission/absorption curve having peaks and valleys at certain characteristic wavelengths. The location of the peak will indicate the type of and the magnitude of the peak will indicate the concentration of the elements, compounds or mixture in the fluid medium.

FIG. 1B is the sectional end view of probe 60 of FIG. 1 taken along section B—B. FIG. 1B shows the relative locations of fiber optics 4 and 5, diaphragm 1 and base 2 and holes 3. The holes 3 provide access to piezoresistive and temperature sensitive elements described below.

FIG. 2A illustrates an embodiment of the electromagnetic reflector 8. To produce effective and desired electromagnetic absorbance and reflectance patterns the diaphragm 1 (FIG. 1) should be transparent to certain electromagnetic wavelengths of the spectrum. That is, the diaphragm 1 should not appreciably affect the absorption curve at those wavelengths. Likewise, the reflector surface 70 should have high reflectivity with respect to absorption so that sufficient waves can be collected for analysis by a spectrometer.

Similarly, the fiber optics 4 and 5 (FIG. 1) should transmit substantially all of the electromagnetic waves. Otherwise, the detected amount of waves will be inaccurate. One arrangement for analyzing electromagnetic waves in the near-infrared to medium-infrared range, and more particularly, from 0.9 microns to 4 microns, provides that the fiber optics 4 and 5 be from about 200 angstroms to about 1000 angstroms in diameter and be constructed of sapphire or another suitable material.

In the illustrated embodiment, reflector 8 is made of stainless steel and has a concave spherical reflector surface 70. Surface 70 is covered with aluminum, gold or silver of anywhere from about 50 angstroms to about 50,000 angstroms thickness. 0f course, the layer can be of another reflective material and/or thicker than this range if desired. The embodiment can achieve an overall transmission efficiency of over 90%.

In polymer melt processing, abrasive and corrosive materials can be encountered. Thus, there is a need to protect the surface 70 from exposure to such materials. Without such protection the surface 70 may degrade from abrasion and corrosion of the polymer or adhesion of the degraded polymer to the surface.

Certain refractory materials, semiconductors and other suitably hard compounds can provide protective coatings for the reflector surface 70. In one embodiment, diamond provides a protective coating. Crystalline, amorphous diamond or diamond like layer can be also deposited on the surface of the reflector surface 70 by conventional growth techniques including plasma enhanced chemical vapor deposition (PECVD).

Diamond's extreme hardness and abrasion resistance make it an excellent protective coating. Diamond is also transparent to a broad wavelength range of electromagnetic waves. Sapphire, silicon carbide, carbon nitride and titanium nitride, and other compounds provide other suitable protective coatings. Favorable results can be achieved when the thickness of the protective coating is from about 0.01 microns to about 5 microns. Of course, the thickness of the coating can be greater than this range if it is desired.

Hard materials such as a diamond or diamond like layer, or a sapphire layer which can be mixed with other elements or compounds so that the surface of the layer will act as an electromagnetic wave reflector yet retain its imperviousness to corrosion and abrasion and other desirable properties.

For example, other additives or alloys that can be used are as follows:

1. Silver, gold, aluminum, rhodium individually or in combination thereof with sapphire, diamond or diamond like material;
2. Carbon nitride;
3. Other suitable additives in a crystalline or amorphous metal oxides, semiconductors or semiconductor like intermetallics, diamond or diamond like materials, wherein an electromagnetic reflective surface results while retaining the other desirable properties.

In another embodiment, the reflector surface 70 includes a plurality of materials for deposited layers. For example, a diamond or diamond like layer can be deposited as the first layer on the concave surface of the reflector 8 of FIG. 2A. Next, an electromagnetic reflecting layer of alumina, silver, chrome, gold, rhodium, titanium nitride and other materials can be deposited on the first layer then an additional diamond layer can be deposited on top of the second layer.

In one embodiment, a first diamond layer from about 0.1 to about 1 microns in thickness is deposited on the concave surface 70 of a reflector 8 made of stainless steel 304. Next, a reflective layer from about 500 to 60,000 angstrom in thickness is deposited on the first diamond layer. Finally, a second diamond layer from about 0.1 to about 1 micron is deposited on the reflective layer. This embodiment will offer the following advantages:

1. Operating temperature capability of up to 800° C.;
2. Electromagnetic transmission range of 0.15 micron to 110 microns; and
3. An efficiency ratio of 70% or higher.

Other suitable materials selected from any crystalline or amorphous metal oxide, semiconductor, intermetallics materials with transmission bandwidth in the electromagnetic wavelength range with good interlayer adhesion and corrosion properties can also produce desired results.

FIG. 2B illustrates a reflector assembly 72 designed to protect the reflector surface 14. The reflector assembly 72 includes a body 74 made of either refractory metal oxides, semiconductors or combinations of thereof such as those used for diaphragm 1 or base 2. These materials are transparent to certain electromagnetic wavelength range and resistant to the abrasion and adhesion of the fluid medium.

Body 74 is a cylindrical shape. However, other shapes can be employed. The body 74 has an electromagnetic reflector 14 disposed on the non-exposed side (i.e., backside) of body 74. The reflector 14 can be made of silver, gold, rhodium or another reflective material. The reflector 14 is disposed between body 74 and a plate 15. The plate 15 is made of metal or the same material used for body 74. The front surface (i.e., opposite the backside) of body 74 faces the fluid medium. The ends of plate 15 extend beyond the ends of body 74 to allow fastening the reflector assembly 72 to the sleeve 9 (FIG. 1).

During operation of the probe 60, the emitted electromagnetic waves transmit through body 74 and impinge on reflector 14 where the waves are reflected back to the diaphragm 1 (FIG. 1) and enter collecting fiber optic 5.

FIG. 3 shows an end view of probe 60. Probe 60 includes a force collecting diaphragm 1, an electromagnetically transparent window 13, piezoresistive elements 12 and temperature sensitive elements 11. Piezoresistive elements 12 and temperature sensitive elements 11 are deposited on diaphragm 1 through epitaxial deposition, chemical vapor deposition, sputtering or some other conventional technique.

The temperature sensitive elements 11 and the piezoresistive elements 12 are preferably epitaxially grown or otherwise deposited on a single crystal or polycrystalline sapphire diaphragm. The piezoresistive elements 12 are grown on an unsupported part near the supported part of a first major surface 80 (FIG. 1) of the diaphragm 1 which faces toward a cavity 66 (FIG. 1) to form a single integral crystal structure with the sapphire diaphragm 1. Alternatively, the piezoresistive elements 12 can be located anywhere on the unsupported part of diaphragm 1.

The piezoresistive elements 12 are from 500 angstroms to 60,000 angstroms thick and preferably from 500 to 7,000 angstroms thick. One piezoresistive material is silicon doped with boron atoms in the range of from $5\times10^{17}$ atoms/cm$^3$ to $2\times10^{21}$ atoms/cm$^3$. In another embodiment, silicon from 8000 to 10,000 angstroms thick can be deposited on the diaphragm 1 and doped with a P-type dopant such as boron atoms in the range of from about $1\times10^{17}$ to about $5\times10^{21}$ atom/cm$^3$ concentration. Additionally, when silicon is used as the piezoresistive material, the silicon can be doped with boron atoms in the range of from $9\times10^{17}$ to $5\times10^{21}$ atoms/cm$^3$ and preferably from $3\times10^{18}$ to $2\times10^{19}$ atoms/cm$^3$.

The doping can be accomplished with standard semiconductor diffusion or ion implantation techniques. Diffusion temperatures in the range of from 1000° C. to 1200° C. can be used when the specified boron concentration is targeted. This provides the piezoresistive elements with a desirable small temperature coefficient of resistance and a relatively large gauge factor.

Other piezoresistive materials include various silicites, nichrome and various cermet materials. The deposited piezoresistive elements are arranged (using standard photolithographic masking and etching techniques) in a Wheatstone bridge configuration with thin conductive traces connecting the piezoresistive elements to contact pads on a sapphire diaphragm.

Other alloys or elements which have demonstrated applicability as piezoresistive elements in pressure sensors, although they lack the high gauge factor of silicon, but have controllable temperature coefficients of resistance are as follows:

1. Pure platinum;
2. Approximately 8% tungsten/balance platinum compounds or other percentages of tungsten;
3. Silicon/platinum compounds, better known as platinum silicites;
4. Nickel/chromium alloys of 20 to 80% chromium and other ratios;
5. Nickel/copper alloys, better known as constantan alloys;
6. Silicon carbide doped with oxygen;
7. Tantalum/aluminum oxide cermets;
8. Aluminum/aluminum oxide cermets;
9. Gold/aluminum oxide cermets;
10. Platinum/aluminum oxide cermets; and
11. Other combinations of the above materials or other materials demonstrating piezoresistive properties on crystalline or amorphous metal oxides or semiconductor substrates.

Other suitable piezoresistive and temperature sensing materials and methods of deposition on a diaphragm are described in U.S. Pat. Nos. 4,994,781 and 5,088,329 to Sahagen. These patents are hereby incorporated by reference.

The connecting arms 76, the contact pads 78, the piezoresistive elements 12 and the temperature sensitive elements 11 shown in FIG. 3 can be made of the same materials. U.S. Pat. Nos. 4,994,781 and 5,088,329 to Sahagen describes use of various materials for the arms, pads and piezoresistive and temperature elements. These patents are hereby incorporated by reference. The various materials can be disposed on a diaphragm 1, for example, of sapphire which can provide a bandpass filter transparent to electromagnetic waves ranging from approximately 0.15 microns to 1000 microns.

Piezoresistive elements 12 are arranged in a Wheatstone bridge on the first major surface 80 (FIG. 1) of diaphragm 1 so that they face toward cavity 66. The fluid medium exerts pressure on a second major surface 82 of diaphragm 1 causing the diaphragm 1 to flex toward the cavity 66. When the voltage across the Wheatstone bridge is held constant, the flexing of the diaphragm 1 generates an electrical signal or change in the electrical current.

As shown in FIG. 3, the electrical signal is conducted through resistive connecting arms 76 to contact pads 78. The pads 78 are welded to leads (not shown) which are threaded through holes 3 (FIG. 1). The leads carry the electrical signal to the outside world. The temperature sensitive elements 11 are located on a supported part of the diaphragm 1. That is where the pressure exerted on the diaphragm 1 results in essentially no flexing. Thus, for the most part, a temperature change will produce a ratiometric electrical signal change which is again sent to external world for analysis through the leads described earlier. Alternatively, the temperature sensitive elements 11 can be disposed at any other part of the first major surface 80 (FIG. 1) of the diaphragm 1.

FIG. 3 illustrates an embodiment where an electromagnetically transparent window 13 is located in the center of the diaphragm 1. Alternatively, the window 13 can be located at another part of the diaphragm 1 or opposite a hole 3 (FIG. 1) capable of containing at least one fiber optic.

For example, an electromagnetic wave source (not shown) can transmit waves through at least one 500 angstrom diameter sapphire fiber optic then through a sapphire diaphragm 1. The waves transmitted into the fluid medium, reflected through a reflector assembly 72 with silver coating on the reflector surface 14 as shown in FIG. 2B and collected through a sapphire fiber optic of 500 angstrom diameter will provide the following:

1. An electromagnetic bandwidth of 0.15 microns to 5 microns;
2. Pressure measurement capability of 50,000 psi;
3. Temperature measurement capability of 1200° C.;
4. Corrosive and abrasive resistant properties; and
5. Other advantages described below.

FIG. 5 illustrates a force collecting diaphragm 1 without the presence of fiber optics when only pressure and temperature measurements are desired. The piezoresistive elements 12 are arranged in a Wheatstone bridge and located inside the cavity on an unsupported area of the first major surface 80 (FIG. 1) of the diaphragm 1 as illustrated. As an alternative, the piezoresistive elements 12 are arranged anywhere on the first major surface 80 (FIG. 1) of diaphragm 1. The temperature sensitive elements 19 and 20 are arranged in a Wheatstone bridge on a supported area of the first major surface 80 (FIG. 1) of diaphragm 1 as illustrated. An alternative arrangement arranges the temperature sensitive elements 19 and 20 anywhere on the first major surface 80 (FIG. 1) of diaphragm 1.

Despite the possibility of placing the temperature elements 19 and 20 anywhere on the first major surface 80, it is preferred to dispose temperature sensitive elements 19 and 20 where there is essentially no flexing of diaphragm 1. In this arrangement, the temperature sensitive elements 19 and 20 will be virtually insensitive to the pressure being exerted on diaphragm 1. Even at this location, residual stresses may still affect the accuracy of the temperature sensitive elements of probe 60.

FIG. 3 illustrates an arrangement for the temperature elements 11 wherein residual stress can be reduced or eliminated by arranging temperature sensitive elements 11 along a 45° angle with respect to the 110 crystallographic axes of silicon.

FIG. 5 illustrates an alternative arrangement to minimize any residual pressure sensitivity of the temperature sensitive elements 19 and 20. Temperature sensitive elements 19 and 20 are arranged in series and perpendicular to each other in a 100 crystallographic plane along the 110 axes on an unsupported area of diaphragm 1. Although temperature sensitive elements 19 and 20 are independently sensitive to minute residual stresses, the stress magnitudes are substantially equal, opposite and cancel each other out resulting in residual stress insensitivity.

FIG. 6 illustrates an electromagnetic window arrangement. A plurality of the holes 3 extend from the upper surface 62 to the lower surface 64 of base 2. In one embodiment, each hole 3 holds at least one fiber optic pair 31 and 32. The fiber optic pair 31 and 32 can perform independent monitoring and analysis of the fluid medium through electromagnetic waves. Diaphragm 1 (e.g., of sapphire) is bonded to base 2 as discussed earlier. The diaphragm 1 provides a plurality of electromagnetic wave windows to seal the holes 3. The windows seal off the upper surface 62 of base 2. One end of the fiber optic pair 31 and 32 makes intimate contact with diaphragm 1. Electromagnetic waves incident in the fluid medium in intimate contact with second major surface 82 of diaphragm 1 are reflected by reflector 8 and collected as before by a collecting fiber optic 32 for analytical and other purposes.

The embodiment shown in FIG. 6 provides means for targeting independent wave bands for specific elements, compounds or mixtures in the fluid medium so that the composition and/or concentration in the fluid medium can be determined. This embodiment has special application as a cost effective compact pollution detector, for example, for use in the automotive industry. Of course, the embodiment would have numerous other applications wherever the quantitative and qualitative analysis of elements, compounds or mixtures is required.

As shown in FIGS. 6 and 6B, similar results can be achieved by installing or depositing bandpass filters 102 inside each hole 3 of base 2 between the ends of fiber optic 31 and 32 and diaphragm 1 or at any other convenient location. For example, the bandpass filter(s) 102 can be placed anywhere between the electromagnetic source and the fluid medium being monitored. Such bandpass filters will help to identify the absorption/transmission curve at the select bandwidths.

FIG. 6A is an end view of the probe of FIG. 6 viewed from the fluid medium side taken on line A—A. FIG. 6A also illustrates additional electromagnetic windows located opposite and aligned with holes, wherein the source and collector fiber optics are used to measure temperature of the fluid medium.

As shown in FIG. 6B, the present invention also provides an embodiment to collect reflected or scattered electromagnetic waves which are focused on a temperature sensitive element 104 on the first major surface 80 of the diaphragm 1. The electromagnetic waves, particularly those in the infrared range, incident on temperature sensitive elements 104 will release additional free electrons which will change the resistance in proportion to the intensity of the incident waves which in turn will detect certain characteristics of the fluid medium such as the composition or identify specific elements, compounds and/or mixtures of the fluid medium. This particular embodiment should have broad application to the automotive industry, for example, as a pollution detector as well as in other industries requiring a relatively inexpensive probe for precise composition analysis of a fluid medium.

FIG. 7 illustrates an approach to maintaining the ends of the fiber optics 33 and the diaphragm 1 (FIG. 7A) in intimate contact with each other. As shown in FIGS. 7 or 7A, the ends 84 of the fiber optics 33 make intimate contact with the first major surface 80 of diaphragm 1. Opposite ends 86 of the fiber optics 33 attach to connectors 38. The fiber optics 33 have slack and are resilient. Because of their resiliency, they are held in compression in the probe 60. Thus, any thermal expansion of the overall package of the probe 60 will cause the resilient fiber optics 33 to extend to the new expanded length of the probe 60 such that they maintain intimate contact with the diaphragm 1. Furthermore, any thermal contraction of the probe 60 will cause the fiber optics 33 to be compressed. In either event, the fiber optics 33 are maintained in intimate contact with diaphragm 1. This approach eliminates the separation of the diaphragm 1 from the ends 84 of fiber optics 33 from either temperature change or flexing of the diaphragm 1. This is important because analysis cannot be reliable unless the ends 84 of fiber optics 33 and diaphragm 1 maintain intimate contact or stay a fixed distance apart.

Figure 8:
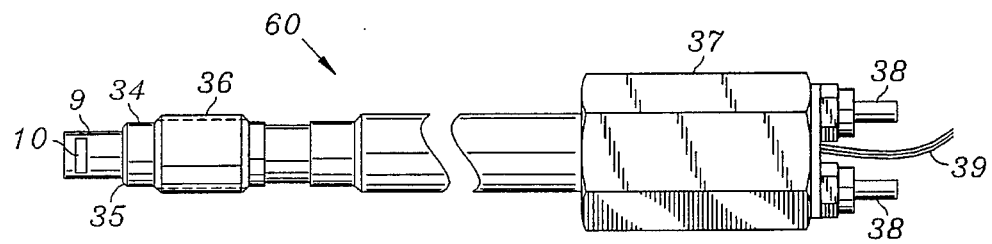
FIG. 8 illustrates the overall assembly of the probe and a location of the fluid medium slot.

FIG. 8 illustrates the overall package of the probe 60 of the present invention. The probe 60 includes a fluid medium slots 10, a external sleeve 9, a hollow ring 34, a body 36, an upper housing 37, connectors 38 and a cable 39.

Figure 9:
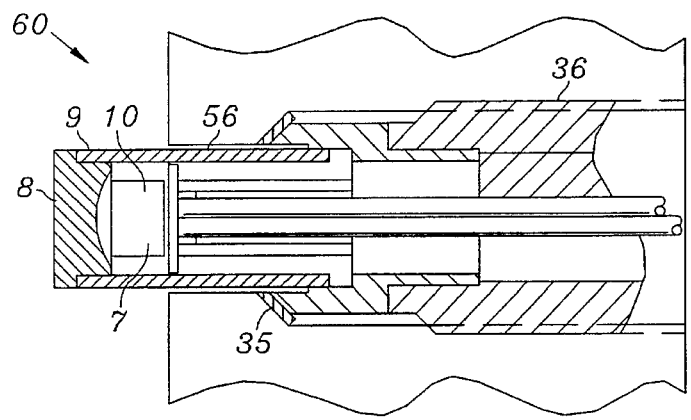
FIG. 9 illustrates the probe in the fluid medium, an isolation slot and an electromagnetic reflector.

FIG. 9 illustrates an embodiment of the probe 60 which isolates the diaphragm 1 from any stress which would prevent obtaining reliable data. FIG. 9 illustrates the probe 60 includes a reflector 8 attached to a sleeve 9 having slots 10 and defining a fluid chamber 7, a sealing tip 35 and an isolation slot 56. The sealing tip 35 seals probe 60 from the fluid medium. A body 36 has threads and exerts a longitudinal force when the tip 35 makes contact with the female portion of the housing 100. The compressive longitudinal force exerted on the tip 35 to seal off the probe 60 from the fluid medium produces residual stress on the diaphragm 1. Isolation slot 56 reduces or eliminates this type of stress from being transferred to the diaphragm 1.

Figure 10:
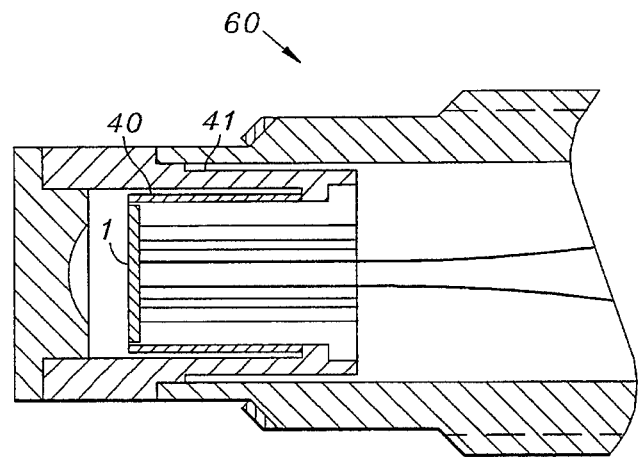
FIG. 10 illustrates an embodiment having a double isolation slot to reduce residual stress of the diaphragm.

FIG. 10 is another embodiment of the probe 60 employing a double isolation slot. An isolation slot 40 coupled with isolation slot 41 further reduces the transfer of residual stress to diaphragm 1. Additional isolation slots (not shown) can be employed if desired to further reduce residual stress.

Figure 11:
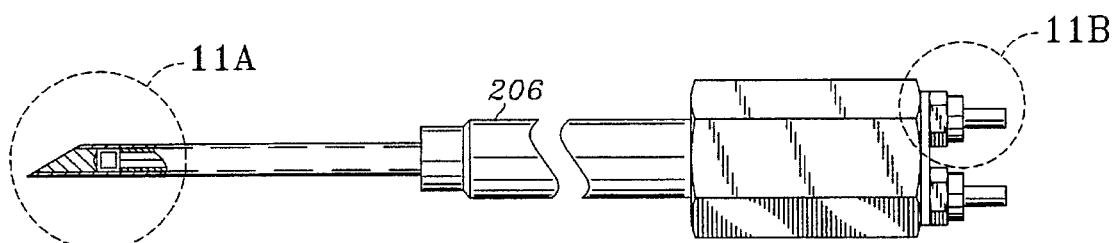
FIG. 11 illustrates an embodiment of the probe where at least one fiber optic is housed in a hypodermic-like housing for medical applications.
Figure 11A:
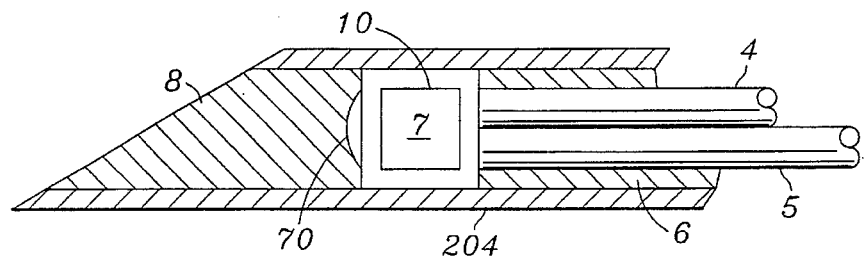
FIG. 11A illustrates the details of the hypodermic needle taken at section A of FIG. 11.

FIG. 11 illustrates still another embodiment of a miniature probe 60 having medical applications and at least one fiber optic housed in a sleeve forming a hypodermic needle. As shown in FIG. 11A, in one embodiment, the probe 60 includes fiber optics 4 and 5 housed in a liner 6 which is in turn housed in a sleeve 204. One side of the sleeve 204 and a reflector 8 form a hypodermic needle for in-vivo application. The sleeve 204 also strengthens the probe 60. The other side of reflector 8 defines one wall of slots 10 and includes a concave reflector surface 70 for reflecting emitted waves from fiber optic 4 into a fluid medium chamber 7. Fiber optic 5 collects the reflected waves and transmits them to the external world for analysis. The medical probe 60 can be of similar material and construction as the probe 60 of FIG. 1 as long as it is not deleterious to the patient. The probe 60 may find use in real-time on-line monitoring of blood, bioreactors, abnormal cell growth and other medical applications.

Figure 11B:
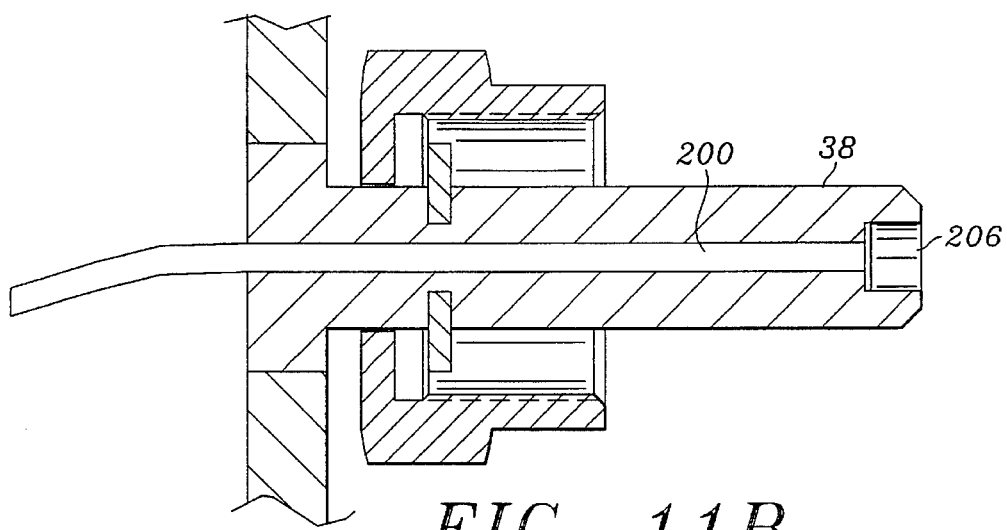
FIG. 11B illustrates the details taken at section B of FIG. 11 where one end of a fiber optic tube opposite the hypodermic needle end is sealed by a window to form a vacuum or gas filled chamber.

FIG. 11B is a close up of section B of FIG. 11 showing a connection for a fiber optic tube 200. The tube 200 exits probe 60 through connector 38 and is sealed by window 206 to form a vacuum or gas filled chamber.

Figure 12:
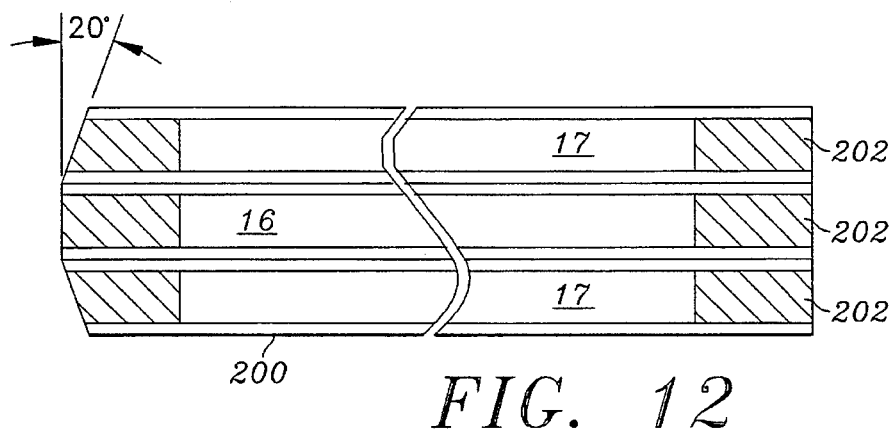
FIG. 12 illustrates the construction of a fiber optic tube making broad electromagnetic wavelength range transmission possible.

FIG. 12 illustrates a fiber optic tube 200 capable of transmitting a broad electromagnetic wavelength range. Crystalline or amorphous refractory, metal oxides, semiconductor material, intermetallics, plastics such as teflon or nylon, or another suitable material can be used to make fiber optic tube 200. Favorable results can be achieved when the tube 200 inner diameter is about 500 microns and the outer diameter is about 600 microns. The ends of tube 200 can be left open to the surroundings or can be sealed with windows 202. The windows 202 can assume a variety of shapes. For example, the windows 202 shown in FIG. 12 is a cone shape derived from a cut across the end of the window such that when it is installed in the tube 200 the end of the window makes an angle of about 20° with respect to a plane perpendicular with the fiber optic axis. This modification will increase the collection efficiency of a fiber optic pair or of a multifiber optic arrangement in that the acceptance cones and corresponding grazing field will increase. When windows 202 seal off the tube 200 at both ends, the tube 200 can be filled with an inert gas or preferably placed under a vacuum. In another embodiment, the ends of the tube 200 can be left open and the tube 200 can form a chamber under a vacuum sealed by diaphragm 1 and window 206.

The tube walls can be made of sapphire, quartz, glass, plastics or any other material suitable for reflecting the electromagnetic waves and having refractive index greater than 1.00. The tube 200 is capable of transmitting electromagnetic waves covering virtually the entire wavelength range from gamma waves, x-rays, infrared, ultra-violet and other wavelengths. In the embodiment using a vacuum, the only apparent limit to a broad wavelength transmission range is the material being used for the windows 202.

The tube 200 transmits a broad electromagnetic wavelength range of transmission not believed possible with conventional fiber materials which limit the transmission bandwidth. For example, conventional fiber optics 4 and 5 can be used to emit and collect waves to monitor cancer cells in the human body, but will not be suitable to transmit x-rays. In contrast, the tube 200 with its broad transmission range may be used to transmit x-ray or other suitable waves for eradication. The tube 200 illustrated in FIG. 12 may be particularly suitable for the transmission of x-rays, gamma rays or other suitable radiation capable of eradicating undesirable cells.

The embodiment described in FIG. 12 provides an added advantage that, unlike hollow metal tubes, the curving of the long fiber optics produced with the present invention will no longer drastically limit the transmission efficiency of the fiber optic.

A metal tube with polished inner walls and plated with gold, silver, platinum, rhodium, aluminum, nickel or another suitable material with greater than 70% reflectivity efficiency can be used. However, a great deal of transmission efficiency will be lost due to the incompatibility of the refractive index, because the slightest curve in the tube will substantially curtail or stop any electromagnetic wave transmission.

What is claimed:

1. A probe for monitoring a fluid pressure, temperature and composition, simultaneously or separately, comprising:

a base having an upper and lower surface, a cavity located along the upper surface, at least one hole extending from the upper to the lower surface;

at least one fiber optic, in the hole, for transmitting an electromagnetic wave;

a diaphragm having a first and second major surface, the first major surface facing the upper surface and the second major surface facing the fluid, wherein the fluid pressure is applied in a direction that causes the diaphragm to flex toward the cavity, wherein the diaphragm is capable of transmitting the electromagnetic wave;

a pressure sensitive element on the diaphragm;

a temperature sensitive element on the diaphragm; and a reflector, spaced from the diaphragm, for reflecting the electromagnetic wave after interaction with the fluid.

2. The probe of claim 1, wherein the base comprises material selected from the group consisting of an amorphous metal oxide, a crystalline metal oxide, a semiconductor material, a metal, and a metal alloy, or a combination thereof, the material having a temperature coefficient of expansion of $1 \times 10^{-7}$/°F. to about $2 \times 10^{-5}$/°F.

3. The probe of claim 1, wherein the base comprises material selected from the group consisting of alumina, diamond, diamond-like material, quartz, beryllium oxide, silicon nitride, a silicon carbide compound, brylia and alumina, MgO and $Al_2O_3$ compounds, zirconium oxide and aluminum oxide systems, $SiO_2$ and aluminum compounds, and silicon nitrate and aluminum oxide compound, or a combination thereof, the material having a temperature coefficient of expansion of $1 \times 10^{-7}/°F.$ to about $2 \times 10^{-5}/°F.$ 4. The probe of claim 1, wherein the diaphragm comprises material selected from the group consisting of an amorphous metal oxide, a crystalline metal oxide, a semiconductor material, intermetallics, and a metal, or a combination thereof, the material having a temperature coefficient of expansion of $1 \times 10^{-7}/°F.$ to about $2 \times 10^{-5}/°F.$ 5. The probe of claim 1, wherein the diaphragm comprises material selected from the group consisting of single crystalline sapphire, polycrystalline sapphire, diamond, diamond-like material, quartz, alumina, beryllium oxide, silicon nitride, silicon carbide compounds, brylia and alumina, MgO and $Al_2O_3$ compounds, zirconium oxide and alumina oxide systems, $SiO_2$ and alumina compounds, and silicon nitrate and aluminum oxide compounds, or a combination thereof, the material having a temperature coefficient of expansion of $1 \times 10^{-7}/°F.$ to about $2 \times 10^{-5}/°F.$ 6. The probe of claim 1, wherein the fiber optic includes a cladding and a core, wherein the cladding comprises material selected from the group consisting of diamond, diamond-like material, and sapphire, or a combination thereof.

7. The probe of claim 1, wherein the reflector comprises a body with a reflective surface and a protective coating disposed on the reflective surface, wherein the protective coating comprises material selected from the group consisting of a crystalline semiconductor, an amorphous semiconductor, a refractory material, a crystalline metal oxide, an amorphous metal oxide, and intermetallics, or a combination thereof, the protective coating being capable of transmitting the electromagnetic wave.

8. The probe of claim 1, wherein the reflector comprises a body including a reflector surface, a reflective layer on the reflector surface, and a protective coating disposed on the reflective layer, wherein the protective coating comprises material selected from the group consisting of crystalline diamond, amorphous diamond, diamond-like material, sapphire, silicon carbide, carbon nitride, and titanium nitride, or a combination thereof.

9. The probe of claim 1, wherein the reflector comprises a body having a reflector surface, a protective reflective layer disposed on the reflector surface, wherein the protective reflective layer includes:

(i) a compound comprises material selected from the group consisting of crystalline diamond, amorphous diamond, diamond-like material, sapphire, carbon nitride, silicon carbide, and titanium nitride, or a combination thereof; and (ii) an additive comprises material selected from the group consisting of silver, gold, aluminum, and rhodium, or a combination thereof.

10. The probe of claim 1, wherein the reflector comprises a reflector assembly, comprising:

a body capable of transmitting the electromagnetic wave and resistant to abrasion, the body having a fluid-facing side and an opposite side;

a plate adjacent the opposite side of the body; and a reflector surface interposed between the body and the plate protecting the reflector surface from the fluid.

11. The probe of claims 7, 8, 9, or 10, further comprising a sleeve housing the base and the diaphragm, strengthening the base and extending beyond the diaphragm to support the reflector.

12. The probe of claim 1, further comprising a bonding layer between the diaphragm and the base, wherein the bonding layer comprises material selected from the group consisting of a glass ceramic, a glass, a metal oxide, and a brazing material, the material having a temperature coefficient of expansion of $1 \times 10^{-7}/°F.$ to about $2 \times 10^{-5}/°F.$ 13. The probe of claim 1, wherein the diaphragm is a single crystalline material having a 100 plane and crystallographic axes of 110 and wherein the temperature sensitive element is disposed on the 100 plane of the diaphragm and includes a longitudinal axis defining a 45 degree angle with respect to the 110 crystallographic axis.

14. The probe of claim 1, wherein the diaphragm is a single crystalline diaphragm having a 100 plane and crystallographic axes of 110, wherein the temperature sensitive element includes:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis which defines a 90 degree angle with respect to the 110 axis.

15. The probe of claim 1, wherein the diaphragm comprises material selected from the group consisting of an amorphous metal oxide and a crystalline metal oxide.

16. A biomedical probe, comprising:

a sleeve forming a hypodermic needle;

a reflector in the sleeve; and at least one fiber optic in the sleeve for emitting and collecting an electromagnetic wave, the fiber optic spaced from the reflector, the fiber optic and the reflector defining a fluid slot, wherein the reflector reflects the emitted wave transmitted through a fluid toward the fiber optic.

17. The probe of claims 1 or 16, wherein the at least one fiber optic comprises a fiber optic surrounded by a plurality of fiber optics.

18. The probe of claim 17, wherein the at least one fiber optic emits the electromagnetic wave and the plurality of fiber optics collect the electromagnetic wave after interaction with the fluid.

19. The probe of claim 17, wherein the at least one fiber optic is adapted to collect the electromagnetic wave after interaction with the fluid and the plurality of fiber optics are adapted to emit the electromagnetic wave.

20. A probe for monitoring a fluid medium, comprising:

a base having an upper surface and a lower surface, and at least one hole extending from the upper to the lower surface for transmitting an electromagnetic wave;

a window having a first and second major surface, wherein the first major surface of the window faces toward the upper surface of the base and the second major surface of the window faces toward the fluid medium being monitored, wherein the window is capable of transmitting the electromagnetic wave; and a reflector, spaced apart from the window, for reflecting the electromagnetic wave after interaction with the fluid medium, wherein the window and the reflector define surfaces of a chamber containing the fluid medium.

21. The probe of claim 20, wherein the base comprises material selected from the group consisting of an amorphous metal oxide, a crystalline metal oxide, a semiconductor material, a metal, and a metal alloy, or a combination thereof, the material having a temperature coefficient of expansion of $1 \times 10^{-7}/°F.$ to about $2 \times 10^{-5}/°F.$ 22. The probe of claim 20, wherein the base comprises material selected from the group consisting of alumina, diamond, diamond-like material, quartz, beryllium oxide, silicon nitride, silicon carbide compounds, brylia and alumina, MgO and $Al_2O_3$ compounds, zirconium oxide and aluminum oxide systems, $SiO_2$ and aluminum compounds, and silicon nitrate and aluminum oxide compounds, a combination thereof, the material having a temperature coefficient of expansion of $1 \times 10^{-7}/°F$. to about $2 \times 10^{-5}/°F$.

23. The probe of claim 20, wherein the window comprises material selected from the group consisting of an amorphous metal oxide, a crystalline metal oxide, a semiconductor material, intermetallics, and a metal, or a combination thereof, the material having a temperature coefficient of expansion of $1 \times 10^{-7}/°F$. to about $2 \times 10^{-5}/°F$.

24. The probe of claim 20, wherein the window comprises material selected from the group consisting of single crystalline sapphire, polycrystalline sapphire, diamond, quartz, alumina, beryllium oxide, silicon nitride, silicon carbide compounds, brylia and alumina, a MgO and $Al_2O_3$ compound, zirconium oxide and alumina oxide systems, $SiO_2$ and alumina compounds, and silicon nitrate and aluminum oxide compounds, the material having a temperature coefficient of expansion of $1 \times 10^{-7}/°F$. to about $2 \times 10^{-5}/°F$.

25. The probe of claim 20, wherein the reflector includes a body having a reflective surface and a protective coating disposed on the reflective surface, wherein the protective coating comprises material selected from the group consisting of a crystalline semiconductor, an amorphous semiconductor, a refractory material, a crystalline metal oxide, an amorphous metal oxide, and intermetallics, or a combination thereof, the protective coating being capable of transmitting the electromagnetic wave.

26. The probe of claim 20, wherein the reflector comprises a body including a reflector surface, a reflective layer on the reflector surface, and a protective coating on the reflective layer, wherein the protective coating comprises material selected from the group consisting of crystalline diamond, amorphous diamond, diamond-like material, sapphire, silicon carbide, carbon nitride, and titanium nitride, or a combination thereof.

27. The probe of claim 20, wherein the reflector comprises a body including a reflector surface and a protective reflective layer disposed on the reflector surface, the protective reflective layer, comprising:

(i) a compound comprises material selected from the group consisting of crystalline diamond, amorphous diamond, diamond-like material, sapphire, carbon nitride, silicon carbide, and titanium nitride, and (ii) an additive comprises material selected from the group consisting of silver, gold, aluminum, and rhodium, or a combination thereof.

28. The probe of claim 20, wherein the reflector comprises:

a body capable of transmitting the electromagnetic wave and resistant to abrasion, the body having a fluid-facing side and an opposite side, a plate adjacent to the opposite side of the body, and a reflector surface interposed between the body and the plate protecting the reflector surface from the fluid medium.

29. The probe of claims 25, 26, 27 or 28, further comprising a sleeve housing the base and the window, strengthening the base, extending beyond the window and supporting the reflector.

30. The probe of claim 20, further comprising a sleeve housing and strengthening the base and the window.

31. The probe of claim 20, further comprising a bonding layer mounting the window to the base, wherein the bonding layer comprises material selected from the group consisting of ceramic glass, glass, a metal oxide, and brazing material, the material having a temperature coefficient of expansion of $1 \times 10^{-7}/°F$. to about $2 \times 10^{-5}/°F$.

32. The probe of claim 20, further comprising a sleeve housing the base and extending beyond the window to support the reflector spaced from the window.

33. The probe of claim 20, further comprising at least one fiber optic residing in the hole for transmitting the wave.

34. The probe of claim 33, wherein the fiber optic includes a cladding and a core, wherein the cladding comprises material selected from the group consisting of diamond and sapphire, or a combination thereof.

35. The probe of claim 20, further comprising a pressure sensitive element on the window.

36. The probe of claim 20, further comprising a temperature sensitive element on the window.

37. The probe of claim 36, wherein the window is a single crystalline material having a 100 plane and crystallographic axes of 110, wherein the temperature sensitive element is disposed on the 100 plane of the window and includes a longitudinal axis defining a 45 degree angle with respect to the 110 crystallographic axis.

38. The probe of claim 36, wherein the window is a single crystalline window having a 100 plane and crystallographic axes of 110, and wherein the temperature sensitive element includes:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis which defines a 90 degree angle with respect to the 110 axis.

39. A biomedical probe, comprising:

a sleeve forming a hypodermic needle;

a reflector in the sleeve;

a fiber optic pair, facing the reflector, wherein at least one fiber of the fiber optic pair is for emitting and at least one fiber is for collecting an electromagnetic wave; and wherein the fiber optic pair spaced from the reflector defines a fluid slot.

40. The biomedical probe of claim 39, further comprising a connector housing a fiber optic of the fiber optic pair and a sealing window adjacent to the connector and to an end of the fiber optic to form a vacuum or gas sealed chamber within the connector.

41. A probe for monitoring a fluid medium, comprising:

a base having an upper and a lower surface, and a plurality of holes extending from the upper to the lower surface;

means for sealing the plurality of holes and transmitting an electromagnetic wave; and a reflector, spaced from the sealing means by the fluid medium, for reflecting the electromagnetic wave after interaction with the fluid medium.

42. The probe of claim 41, further comprising a first fiber optic in at least one hole.

43. The probe of claim 42, further comprising a second fiber optic, wherein the first fiber optic emits the electromagnetic wave into the fluid medium and the second fiber optic collects the electromagnetic wave after interaction with the fluid medium.

44. The probe of claim 42, further comprising a temperature sensitive element adjacent a surface of the window facing away from the fluid medium and toward the first fiber optic.

45. The probe of claim 41, further comprising a plurality of fiber optics in at least one hole.

46. The probe of claim 41, wherein the sealing means includes an individual window for each hole.

47. The probe of claim 41, wherein the sealing means includes a window for all of the plurality of holes.

48. The probe of claim 41, wherein the sealing means includes means for filtering independent wave bands to identify specific elements, compounds or mixtures in the fluid medium.

49. The probe of claim 41, wherein the sealing means includes a bandpass filter disposed in the path of the electromagnetic wave for filtering a wave band to identify an element, a compound or a mixture in the fluid medium.

50. The probe of claim 49, wherein the bandpass filter is disposed between an electromagnetic source and the sealing means.

51. A probe for monitoring a fluid medium, comprising:
   a base having an upper surface and a lower surface, and a cavity located along the upper surface, and at least one hole extending from the upper to the lower surface for transmitting an electromagnetic wave;
   at least one fiber optic in the hole for emitting and collecting the wave;
   a window having a first major surface and a second major surface, wherein the first major surface of the window faces toward the upper surface of the base and the second major surface of the window faces toward the fluid medium, wherein a pressure of the fluid medium is applied in a direction that causes the window to flex toward the cavity in the base and wherein the window is capable of transmitting the electromagnetic wave; and
   a reflector, spaced apart from the window, for reflecting the electromagnetic wave after interaction with the fluid medium.

52. The probe of claim 51, wherein the base comprises material selected from the group consisting of an amorphous metal oxide, a crystalline metal oxide, a semiconductor material, a metal, and a metal alloy, or a combination thereof, the material having a temperature coefficient of expansion of $1 \times 10^{-7}/°F$. to about $2 \times 10^{-5}/°F$.

53. The probe of claim 51, wherein the base comprises material selected from the group consisting of alumina, diamond, diamond-like material, quartz, beryllium oxide, silicon nitride, silicon carbide compounds, brylia and alumina, MgO and $Al_2O_3$ compounds, zirconium oxide and aluminum oxide systems, $SiO_2$ and aluminum compounds, and silicon nitrate and aluminum oxide compounds, or a combination thereof, the material having a temperature coefficient of expansion of $1 \times 10^{-7}/°F$. to about $2 \times 10^{-5}/°F$.

54. The probe of claim 51, wherein the window comprises material selected from the group consisting of an amorphous metal oxide, a crystalline oxide, a semiconductor material, intermetallics, and a metal, or a combination thereof, the material having a temperature coefficient of expansion of $1 \times 10^{-7}/°F$. to about $2 \times 10^{-5}/°F$.

55. The probe of claim 51, wherein the window comprises material selected from the group consisting of single crystalline sapphire, polycrystalline sapphire, diamond, diamond-like material, quartz, alumina, beryllium oxide, silicon nitride, silicon carbide compounds, brylia and alumina, MgO and $Al_2O_3$ compounds, zirconium oxide and alumina oxide systems, $SiO_2$ and alumina compounds, and silicon nitrate and aluminum oxide compounds, the material having a temperature coefficient of expansion of $1 \times 10^{-7}/°F$. to about $2 \times 10^{-5}/°F$.

56. The probe of claim 51, wherein the reflector includes a body with a reflective surface and a protective coating disposed on the reflective surface, wherein the protective coating comprises material selected from the group consisting of a crystalline semiconductor, an amorphous semiconductor, a refractory material, a crystalline metal oxide, an amorphous metal oxide, and intermetallics, or a combination thereof, the protective coating being capable of transmitting the electromagnetic wave.

57. The probe of claim 51, wherein the reflector comprises a body including a reflector surface, a reflective layer on the reflector surface, and a protective coating on the reflective layer, wherein the protective coating comprises material selected from the group consisting of crystalline diamond, amorphous diamond, diamond-like material, sapphire, silicon carbide, carbon nitride, and titanium nitride, or a combination thereof.

58. The probe of claim 51, wherein the reflector comprises a body including a reflector surface, and a protective reflective layer, disposed on the reflector surface, the protective reflective layer, comprising:
   (i) a compound comprises material selected from the group consisting of crystalline diamond, amorphous diamond, diamond-like material, sapphire, carbon nitride, silicon carbide, and titanium nitride, and
   (ii) an additive comprises material selected from the group consisting of silver, gold, aluminum, and rhodium, or a combination thereof.

59. The probe of claim 51, wherein the reflector comprises a reflector assembly, comprising:
   a body capable of transmitting the electromagnetic wave and resistant to abrasion, the body having a fluid-facing side and an opposite side,
   a plate adjacent the opposite side of the body, and
   a reflector surface interposed between the body and the plate protecting the reflector surface from the fluid medium.

60. The probe of claims 56, 57, 58 or 59, further comprising a sleeve housing the base and the window, strengthening the base, extending beyond the window and supporting the reflector.

61. The probe of claim 51, further comprising a sleeve housing and strengthening the base and the window.

62. The probe of claim 51, further comprising a bonding layer, the window mounted to the base by the bonding layer comprises material selected from the group consisting of ceramic glass, glass, a metal oxide, and a brazing material, the material having a temperature coefficient of expansion of $1 \times 10^{-7}/°F$. to about $2 \times 10^{-5}/°F$.

63. The probe of claim 51, further comprising a sleeve housing the base, extending beyond the window, and supporting the reflector spaced from the window.

64. The probe of claim 51, wherein the at least one fiber optic in the hole is surrounded by a plurality of fiber optics.

65. The probe of claim 64, wherein the at least one fiber optic includes a fiber optic adapted to emit the electromagnetic wave and wherein the plurality of fiber optics are adapted to collect the electromagnetic wave after interaction with the fluid medium.

66. The probe of claim 64, wherein the one fiber optic collects the electromagnetic wave after interaction with the fluid medium and the plurality of fiber optics are adapted to emit the electromagnetic wave.

67. The probe of claim 51, wherein the fiber optic includes a cladding and a core, wherein the cladding comprises material selected from the group consisting of diamond and sapphire, or a combination thereof.

68. The probe of claim 51, wherein the window is a single crystalline material having a 100 plane and crystallographic axes of 110 and further comprising at least one temperature sensitive element disposed on the 100 plane of the window and including a longitudinal axis defining a 45 degree angle with respect to the 110 crystallographic axis.

69. The probe of claim 51, wherein the window is a single crystalline window having a 100 plane and crystallographic axes of 110 and further comprising:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis which defines a 90 degree angle with respect to the 110 axis.

70. The probe of claims 20 or 51, wherein the window comprises material selected from the group consisting of an amorphous metal oxide and a crystalline metal oxide.

71. The probe of claims 1, 33, or 51, wherein the at least one fiber optic includes a cladding and a core, wherein the cladding comprises material selected from the group consisting of crystalline refractory materials, amorphous refractory materials, metal oxides, semiconductor material, intermetallics, and a plastic, or a combination thereof.

72. The probe of claims 1, 20, or 51, wherein the base comprises material selected from the group consisting of an amorphous metal oxide and a crystalline metal oxide.

73. The probe of claims 1, 20, or 51, wherein the reflector comprises a body having a reflector surface, a protective reflective layer disposed on the reflector surface, wherein the protective reflective layer includes:

(i) a compound comprises material selected from the group consisting of a crystalline metal oxide, an amorphous metal oxide, a refractory material, intermetallics, a crystalline semiconductor, and an amorphous semiconductor, or a combination thereof; and (ii) an additive comprises material selected from the group consisting of silver, gold, aluminum, and rhodium, or a combination thereof.

74. The probe of claims 1, 20, or 51, wherein the reflector comprises a body with a reflective surface and a protective coating disposed on the reflective surface, wherein the protective coating comprises material selected from the group consisting of crystalline diamond, amorphous diamond, diamond-like material, sapphire, silicon carbide, carbon nitride, and titanium nitride, or a combination thereof, the protective coating being capable of transmitting the electromagnetic wave.

75. The probe of claims 1, 20, or 51, wherein the reflector comprises a body including a reflector surface, a reflective layer on the reflector surface, and a protective coating disposed on the reflective layer, wherein the protective coating comprises material selected from the group consisting of crystalline semiconductor, an amorphous semiconductor, a refractory material, a crystalline metal oxide, an amorphous metal oxide, and intermetallics, or a combination thereof, the protective coating being capable of transmitting the electromagnetic wave.

76. A probe for monitoring a fluid medium, comprising:

a base having at least one hole;

a window, disposed across the hole, capable of transmitting an electromagnetic wave; and a reflector in the fluid medium, spaced apart from the window, disposed to reflect the electromagnetic wave after interaction with the fluid medium.

77. The probe of claim 76, further comprising at least one fiber optic in the hole.

78. A probe for monitoring a fluid pressure, temperature and composition, simultaneously or separately, comprising:

a pressure cell base having an upper and lower surface, a cavity located along the upper surface, at least one hole extending from the upper surface to the lower surface;

a fiber optic in the hole;

a sapphire force collector diaphragm having first and second major surfaces, mounted on the pressure cell base over the cavity, so that the first major surface faces toward the upper surface of the base and the second major surface faces toward the fluid being monitored so that the pressure of the fluid is applied in a direction that causes the diaphragm to flex toward the base;

a silicon layer, formed on the first major surface of the diaphragm, doped with P-type or N-type dopant atoms; and a temperature sensitive element.

79. The probe of claim 78, wherein the diaphragm is a single crystalline material having a 100 plane and crystallographic axes of 110 and the temperature sensitive element is disposed on the 100 plane of the diaphragm and includes a longitudinal axis defining a 45 degree angle with respect to the 110 crystallographic axis.

80. The probe of claim 78, wherein the diaphragm is a single crystalline diaphragm having a 100 plane and crystallographic axes of 110, the temperature sensitive element including:

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis defining a 90 degree angle with respect to the 110 axis.

81. A probe for monitoring a fluid pressure, temperature and composition, simultaneously or separately, comprising:

a pressure cell base having an upper and lower surface, a cavity located along the upper surface, at least one hole extending from the upper surface to the lower surface;

at least a fiber optic pair, in the hole, for emitting and collecting an electromagnetic wave;

a force collector diaphragm having first and second major surfaces, mounted on the pressure cell base over the cavity, so that the first major surface faces toward the upper surface of the base and the second major surface faces toward the fluid being monitored so that the pressure of the fluid is applied in a direction that causes the diaphragm to flex toward the base, wherein the diaphragm is a single crystalline diaphragm having a 100 plane and crystallographic axes of 110;

at least one wheatstone bridge formed on the first major surface of the diaphragm, wherein the bridge is doped with P-type or N-type dopant atoms;

a first temperature sensitive element disposed on the 100 plane; and a second temperature sensitive element in series with the first element and disposed on the 100 plane, wherein the first element includes a first longitudinal axis on the 110 axis and the second element includes a second longitudinal axis defining a 90 degree angle with respect to the 110 axis.

82. A probe for monitoring a fluid pressure, temperature and composition, simultaneously or separately, comprising:

an alumina pressure cell base having an upper and lower surface, a cavity located along the upper surface, at least one hole extending from the upper surface to the lower surface;

at least a fiber optic pair, in the hole, at least one fiber optic for emitting and the other fiber optic for collecting an electromagnetic wave;

a sapphire force collector diaphragm having first and second major surfaces, mounted on the pressure cell base over the cavity, so that the first major surface faces toward the upper surface of the base and the second major surface faces toward the fluid being monitored so that the pressure of the fluid is applied in a direction that causes the diaphragm to flex toward the base, wherein the diaphragm is a single crystalline diaphragm having a 100 plane and crystallographic axes of 110;

at least one silicon wheatstone bridge formed on the first major surface of the diaphragm, wherein the bridge is doped with P-type dopant atoms;

a first silicon temperature sensitive element doped with P-type dopant atoms disposed on the 100 plane; and a second temperature sensitive element doped with P-type dopant in series with the first element and disposed on the 100 plane, wherein the first element includes a first longitudinal axis on the 110 axis and the second element includes a second longitudinal axis defining a 90 degree angle with respect to the 110 axis.

83. A probe for monitoring a fluid pressure, temperature and composition, simultaneously or separately, comprising:

a base having an upper and lower surface, a cavity located along the upper surface, at least one hole extending from the upper to the lower surface;

means, in the hole, for transmitting an electromagnetic wave;

a diaphragm having a first and second major surface, the first major surface facing the upper surface and the second major surface facing the fluid, wherein a fluid pressure is applied in a direction that causes the diaphragm to flex toward the cavity, wherein the diaphragm is capable of transmitting the electromagnetic wave;

a pressure sensitive element on the diaphragm;

a temperature sensitive element on the diaphragm; and a reflector, spaced from the diaphragm, for reflecting the electromagnetic wave.

* * * * *